US00PP29070P3

(12) United States Plant Patent
Hansen et al.

(10) Patent No.: US PP29,070 P3
(45) Date of Patent: Mar. 6, 2018

(54) ***MISCANTHUS* PLANT NAMED 'ENCORE'**

(50) Latin Name: ***Miscanthus sinensis* (Andersson)**
Varietal Denomination: Encore

(71) Applicants: Hans A. Hansen, Zeeland, MI (US); Kevin A. Hurd, Austin, TX (US)

(72) Inventors: Hans A. Hansen, Zeeland, MI (US); Kevin A. Hurd, Austin, TX (US)

(73) Assignee: Walters Gardens, Inc., Zeeland, MI (US)

( * ) Notice: Subject to any disclaimer, the term of this patent is extended or adjusted under 35 U.S.C. 154(b) by 55 days.

(21) Appl. No.: 14/999,483

(22) Filed: May 12, 2016

(65) Prior Publication Data

US 2017/0332538 P1 Nov. 16, 2017

(51) Int. Cl.
*A01H 5/12* (2006.01)

(52) U.S. Cl.
USPC ..... Plt./384
CPC ..... *A01H 5/12* (2013.01)

(58) Field of Classification Search
USPC ..... Plt./384
See application file for complete search history.

*Primary Examiner* — Keith O Robinson

(57) ABSTRACT

A new and distinct cultivar of ornamental *Miscanthus sinensis* plant named 'Encore' useful in the landscape en masse, small group or single specimen with dense upright culms and arching foliage having dark green color and near-white midribs. The flower habit is open and at varying heights creating a rounded dome outline beginning in early fall with repeat flush about two to three weeks later, and effective through the winter.

1 Drawing Sheet

Latin botanical classification: *Miscanthus sinensis* (Andersson).

Variety denomination: 'Encore'.

BACKGROUND OF THE NEW PLANT

The present invention relates to the new and distinct plant cultivar of *Miscanthus sinensis* named 'Encore', hereinafter also referred to as 'Encore' and the "new plant" which represents a new and distinct cultivar of ornamental maiden grass for landscape and cut foliage and flower use. The seed was the result of open pollination between *Miscanthus sinensis* 'Huron Sunrise' (not patented) as the female or seed parent and the male or pollen parent is unknown but may have been any one of a number of cultivar or seedling selections in the breeding area. Seed was collected by the inventors on Jan. 11, 2010 at a wholesale perennial nursery in Zeeland, Mich., USA. During initial evaluation in the summer of 2011 and afterward the individual seedling was assigned the breeder code of HK10-06-02. Final evaluation of the new plant was performed at the same nursery in Zeeland, Mich. during the summer and fall of 2013.

The new plant has been successfully asexually propagated by division and sterile shoot plant tissue culture at the same perennial plant nursery in Zeeland, Mich. and found to produce stable and identical plants that maintain the unique characteristics of the original plant. The plant is stable and reproduces true-to-type in successive generations of asexual reproduction.

No plants of *Miscanthus sinensis* 'Encore' have been sold, in this country or anywhere in the world, prior to the filing of this application, nor has any disclosure of the new plant been made prior to the filing of this application with the except of that which was disclosed within one-year period of the filing of this application and was either derived directly or indirectly from the inventor.

*Miscanthus* 'Encore' differs from its parents as well as all other *Miscanthus* known to the applicant. The new plant differs from the seed parent *Miscanthus* 'Huron Sunrise' primarily in the new plant having taller habit and extended flowering period beginning to flower earlier and repeating with a second set of flowers. The seed heads of 'Encore' are also lighter creamy tan compared to the medium tan of 'Huron Sunrise'.

Compared to 'Autumn Anthem' U.S. Plant Pat. No. 27,411 the new plant is taller and produces flowers at staggering periods. Compared to 'Gracillimus' (not patented), the new plant has broader foliage and flowers at staggering times. Compared to 'Morning Light' (not patented) the new plant has narrower foliage and flowers both earlier in the season and later, too. All of the above listed comparison cultivars also flower in one distinct season unlike 'Encore' that repeat flowers with more than one distinctive season.

BRIEF SUMMARY OF THE NEW PLANT

The new plant is different from all *Miscanthus sinensis* cultivars known to the applicant in the following combined traits:

1. Dense upright crams with linear arching foliage.
2. Leaves of dark green with a wide near-white midrib.
3. Initial flowers in early fall with repeat flush about two to three weeks later and seed heads remain effective through the winter.
4. Flowering habit is open and at varying heights creating a rounded dome outline.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, intensity, source and direction may cause the appearance of minor variation in color. The plant in the photographs is a three-year old plant grown in full-sun trial garden.

DETAILED BOTANICAL DESCRIPTION

Figure 1:
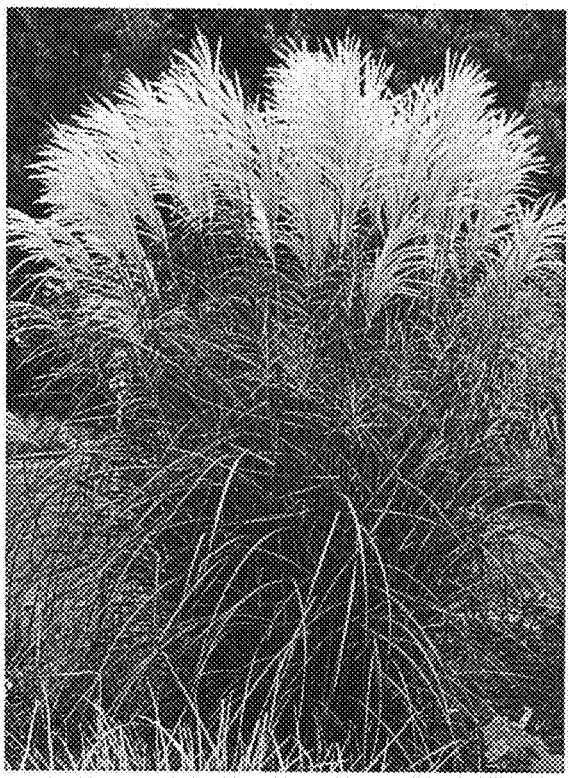
FIG. 1 shows the overall plant in mid fall with two layers of flowers.
Figure 2:
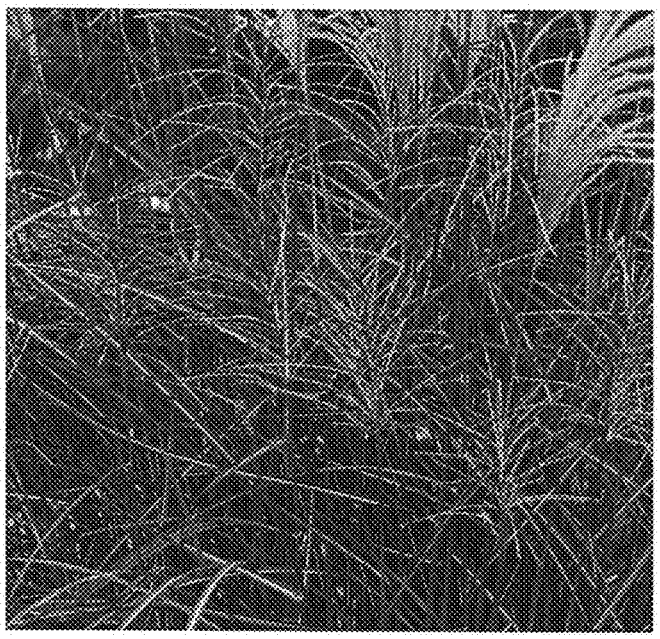
FIG. 2 shows a close-up of the early inflorescence in early-fall.

The following descriptions and color references are based on the 2001 edition of The Royal Horticultural Society Colour Chart except where common dictionary terms are used. The new plant, 'Encore', has not been observed under all possible environments. The phenotype may vary slightly with different environmental conditions, such as temperature, light, fertility, moisture and maturity levels, but without any change in the genotype. The following observations and size descriptions are of a three-year old plant in a trail garden in Zeeland, Mich. in full sun with supplemental water and fertilizer.

Parentage: *Miscanthus sinensis* 'Huron Sunrise' (not patented) (female, seed) times unknown pollen male parent.

Propagation method: By division of the culms and by shoot tissue culture.

Time to finishing in a three-liter pot: About three months.

Vigor: Rapid.

Rooting habit: Normal, fibrous, coarse, branching.

Plant description: Winter-hardy herbaceous perennial forming tightly rhizomatous clump, with upright culms and arching leaves producing a medium landscape texture through summer and fine flowering texture through winter.

Plant size: Foliage height before flowering is about 125 to 135 cm tall from soil line to the top of the leaves and about 35 to 45 cm wide at soil line, about 150 cm to 165 cm wide at about 110 cm above soil line, and about 140 to 195 cm tall to top of flowers.

Foliage description: Glaucous, glabrous adaxial, and abaxial glaucous and sparsely pubescent with adpressed hairs; margin entire except microscopically serrulate; linear; conduplicate along center vein; alternate; arching from sheath to apex; sheathed from node of attachment to ligule; deciduous but persist through winter; about ten leaves per culm.

Foliage size: Total length to about 85.0 cm long, averaging about 75.0 cm; length of sheath average about 16.0 cm, average length of blade about 59.0 cm long; average about 7.0 mm wide.

Foliage color: Young expanding foliage nearest RHS 144A both adaxial and abaxial surfaces; adaxial mature between RHS 138A and RHS 138B, abaxial mature nearest RHS 138B; adaxial and abaxial winter color between RHS 165D and RHS 165C.

Color at ligule: Between RHS 151D and RHS 145C.

Veins: Parallel; center vein about 3.0 mm wide.

Vein color: Center vein nearest RHS 155C adaxial and abaxial; other minor veins same as the surrounding leaf on both adaxial and abaxial surfaces.

Culm: Glaucous; glabrous; erect terete; completely enclosed by leaf sheath; about 100 to 115 cm long to panicles and about 5.0 mm diameter at base; internode length 5 to 10 cm, shorter near base, average about 6.3 cm.

Culm color: Nearest RHS 146D.

Nodes: Swollen, lower nodes to about 7.0 mm diameter, glabrous; covered by sheath.

Node color: Blend between RHS 191A and RHS 197A.

Ligule: Fringed membranous, 2.0 mm long and as wide as leaf; with fine hairs to 5.0 mm long.

Ligule color: Between RHS 151ID and RHS 145C; drying to nearest RHS 165D; hair color nearest RHS 155D.

Flower description: Spikelets in pairs on branched panicle; one panicle per culm; beginning mid-September; drying on plant but persisting through winter; no fragrance detected.

Panicle: About 28 to 30 cm long, about 18 to 22 cm wide at widest portion; with about 20 branches or racemes; branches or racemes to about 17.0 cm long; attitude upward.

Panicle color: Beginning nearest RHS 176C and developing to between RHS 161C and RHS 159B.

Spikelet: With tufts of fine hairs extending radially about 5.0 mm long and about 0.1 mm diameter at base and along sides of paired glumes.

Pedicle: About 2.5 mm long and less than 0.5 mm diameter; color nearest RHS 165C.

Lemma: Of about equal size and color to palea; about 4.0 mm long and about 1.0 mm wide; base truncate with tufts of hairs; apex narrowly acute; margin entire with hairs of equal size to basal tuft; color nearest RHS 164C; hair color collectively nearest RHS 158C.

Palea: Matched to lemma in size, shape, hairs and color.

Awn: Thin, bristle, about 4.0 mm long; color between RHS 164C and RHS 164B.

Gynoecium: Two.

*Stigma*.—Two, plumose, protruding about 2 mm from glume; color nearest RHS 183C.

Androecium:

*Filaments*.—Fine, hair-like, white, about 2.0 mm long and about 0.3 mm diameter; lighter than RHS 155D.

*Anthers*.—Oblong; about 2.0 mm long and 1.0 mm diameter; color nearest RHS 183B.

*Pollen*.—Abundant; color nearest RHS 16C.

Fruit: Caryopsis; enclosed in glume; about 2 to 3 mm long and about 0.5 mm diameter, nearest RHS 164C.

Hardiness, pest and disease resistance: The new plant grows best with plenty of moisture and adequate drainage, but is able to tolerate considerable drought when established. Hardiness at least from USDA zone 5 through 9. Disease and pest resistance beyond what is typical of that of other maiden grasses has not been observed.

The invention claimed is:

1. A new and distinct cultivar of ornamental *Miscanthus sinensis* plant named 'Encore' as herein described and illustrated.

* * * * *